(12) United States Patent
Brown

(10) Patent No.: US 10,357,678 B2
(45) Date of Patent: Jul. 23, 2019

(54) MAGNETIC EXERCISE ANCHOR

(71) Applicant: Bryant Brown, Raleigh, NC (US)

(72) Inventor: Bryant Brown, Raleigh, NC (US)

( * ) Notice: Subject to any disclaimer, the term of this patent is extended or adjusted under 35 U.S.C. 154(b) by 166 days.

(21) Appl. No.: 15/014,195

(22) Filed: Feb. 3, 2016

(65) Prior Publication Data

US 2016/0256726 A1    Sep. 8, 2016

Related U.S. Application Data

(60) Provisional application No. 62/112,442, filed on Feb. 5, 2015.

(51) Int. Cl.

| | | |
|---|---|---|
| *A61B 5/00* | (2006.01) | |
| *A61B 5/22* | (2006.01) | |
| *A63B 21/00* | (2006.01) | |
| *A63B 21/02* | (2006.01) | |
| *A63B 21/04* | (2006.01) | |
| *A63B 21/16* | (2006.01) | |
| *A63B 23/04* | (2006.01) | |
| *A63B 23/12* | (2006.01) | |

(Continued)

(52) U.S. Cl.
CPC .......... *A63B 21/0442* (2013.01); *A61B 5/486* (2013.01); *A63B 21/00061* (2013.01); *A63B 21/0552* (2013.01); *A63B 21/0557* (2013.01); *A63B 21/16* (2013.01); *A63B 21/4013* (2015.10); *A63B 21/4043* (2015.10); *A63B 23/03541* (2013.01); *A63B 23/0482* (2013.01); *A63B 23/1209* (2013.01); *A61B 5/224* (2013.01); *A63B 21/00069* (2013.01); *A63B 21/023* (2013.01); *A63B 23/0355* (2013.01); *A63B 23/03575* (2013.01); *A63B 23/047* (2013.01); *A63B 2209/02* (2013.01); *A63B 2209/08* (2013.01); *A63B 2220/17* (2013.01); *A63B 2220/24* (2013.01); *A63B 2220/31* (2013.01); *A63B 2220/51* (2013.01); *A63B 2220/833* (2013.01)

(58) Field of Classification Search
CPC ..... A63B 21/0442; A63B 21/16; A63B 5/486; A63B 21/00061; A63B 21/0552; A63B 23/03541; A63B 23/0482; A63B 23/1209; A63B 21/4013; A63B 21/4034; A63B 21/05–0557; A63B 21/4035; A63B 21/4043; A63B 21/023; A63B 23/03575; A63B 23/0355; A63B 2220/31; A63B 23/047; A63B 2209/08; A63B 2220/833; A63B 21/00069; A63B 2220/17; A63B 2209/02; A63B 2220/24; A63B 2220/51; A61B 5/224
USPC ............... 482/1–9, 92–94, 98–103, 121–139
See application file for complete search history.

(56) References Cited

U.S. PATENT DOCUMENTS

| | | | | |
|---|---|---|---|---|
| 3,708,234 A | * | 1/1973 | Fukuda | B43K 1/08 |
| | | | | 401/216 |
| 3,781,047 A | * | 12/1973 | Surko, Jr. | E05C 17/56 |
| | | | | 292/251.5 |

(Continued)

*Primary Examiner* — Garrett K Atkinson
(74) *Attorney, Agent, or Firm* — Cranfill Sumner & Hartzog, LLP; Russell Racine

(57) ABSTRACT

The Magnetic Exercise Anchor is an exercise device providing an attachment point to anchor resistance bands to a metallic structure, wherein the exercise apparatus includes a series of magnets working as an anchor to serve as an attachment point, which may temporarily affix the device and resistance bands to a metal surface.

7 Claims, 4 Drawing Sheets

(51) Int. Cl.
*A63B 21/055* (2006.01)
*A63B 23/035* (2006.01)

(56) References Cited

U.S. PATENT DOCUMENTS

| | | | | |
|---|---|---|---|---|
| 3,810,550 | A * | 5/1974 | Longarzo | B43M 99/003 |
| | | | | 211/69.6 |
| 3,891,221 | A * | 6/1975 | Gordon | A63B 63/00 |
| | | | | 273/456 |
| 4,719,549 | A * | 1/1988 | Apel | F21S 2/00 |
| | | | | 362/398 |
| 5,051,638 | A * | 9/1991 | Pyles | A63B 21/0051 |
| | | | | 310/105 |
| 5,306,217 | A * | 4/1994 | Bracone | A63B 1/00 |
| | | | | 4/496 |
| 6,077,175 | A * | 6/2000 | Fearnow | A63B 69/0013 |
| | | | | 473/468 |
| 6,245,002 | B1 * | 6/2001 | Beliakov | A63B 21/00192 |
| | | | | 482/148 |
| 6,599,321 | B2 * | 7/2003 | Hyde, Jr. | A61B 17/68 |
| | | | | 623/18.12 |
| 7,163,181 | B2 * | 1/2007 | Omps | F16C 11/0619 |
| | | | | 248/181.1 |
| 7,170,285 | B2 * | 1/2007 | Spratte | B60G 7/005 |
| | | | | 324/207.21 |
| 7,841,799 | B2 * | 11/2010 | Spratte | F16C 11/0604 |
| | | | | 403/122 |
| 9,242,160 | B2 * | 1/2016 | Tyndall | A63B 69/0013 |
| 9,674,411 | B2 * | 6/2017 | Cover | H04N 5/2252 |
| 2002/0032484 | A1 * | 3/2002 | Hyde, Jr. | A61B 17/68 |
| | | | | 623/18.12 |
| 2004/0067096 | A1 * | 4/2004 | Ersoy | B60G 7/005 |
| | | | | 403/137 |
| 2004/0100357 | A1 * | 5/2004 | Kruse | B60G 7/005 |
| | | | | 338/128 |
| 2004/0118985 | A1 * | 6/2004 | Omps | F16C 11/0619 |
| | | | | 248/181.1 |
| 2006/0078369 | A1 * | 4/2006 | Spratte | B60G 7/005 |
| | | | | 403/122 |
| 2007/0107339 | A1 * | 5/2007 | Matsumoto | E02D 27/32 |
| | | | | 52/295 |
| 2010/0217325 | A1 * | 8/2010 | Hochschuler | A61B 17/864 |
| | | | | 606/264 |
| 2015/0381859 | A1 * | 12/2015 | Cover | H04W 84/12 |
| | | | | 348/374 |

* cited by examiner

MAGNETIC EXERCISE ANCHOR

CROSS-REFERENCE TO RELATED APPLICATIONS

This application claims priority to provisional application No. 62/112,442 filed Feb. 5, 2015.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Physical fitness and exercise is becoming increasingly popular as people understand that being physically active aids in overall health and prevention of disease. Many programs and devices have been formulated and manufactured to aid people in becoming more physically fit and active. Also, activities such as running, swimming, and even walking have grown in popularity as the population has grown more health conscious. Many of these activities work quite well when participated in regularly. However, basic strength training remains one of the best ways to maintain physical health and keep high levels of fitness.

Strength training can be achieved in many different ways. However, when brought down to the most fundamental state, strength training involves exerting muscle force against an object. By doing this, the muscle is forced to contract in order to exert force against something. In weight lifting, for example, the muscle is contracted in order to move the weight, then is relaxed in order to allow the weight to return to its starting position. Repeated movements against the weight strengthen the muscle. This fundamental mechanic can be altered by changing the amount of weight, the number of repetitions of the movement, the distance over which the weight is moved, etc. Further, this fundamental exercise can also function to move the body instead of the weight. For example, when a person does a push up, the weight is actually the person's body and the muscle contraction is used to push the body up and away from the surface. Thus, the weight of the body functions as a weight to be lifted by pushing against an immovable object, in this case the floor.

Essentially, whenever a muscle contracts and meets with any resistance, it exercises the muscle. Repeated movements can function to strengthen the muscle. Thus, the ability to contract the muscle against a weight is necessary to promote exercise of the muscle and realize the health benefits of such activity.

One popular method of strength training is the use of what are known as resistance bands. These bands are essentially giant rubber bands that stretch under force. A person exercising with resistance bands will affix the band to a stationary object and pull or push against the band in order to flex or stretch the band. Because of the elasticity of the resistance band, it becomes increasingly difficult to stretch the band the further it is stretched. In other words, the force necessary to stretch the band increases as the band is stretched. Also, many different bands are available in varying strengths. So, a beginner can use a resistance band that is easy to stretch while a stronger person can use a band that takes significantly more force to stretch.

Advantages of using resistance bands include the fact the bands are relatively inexpensive. Because the bands are essentially rubber bands, one can usually purchase multiple bands to cover a wide variation of resistance. Also, use of resistance bands does not require a large area in which to exercise. One does not need to go to the gym to use resistance bands; one can use them anywhere.

One requirement to using the resistance bands for exercising is that the band must be able to stretch which means that it must be secured on both ends to something. In some cases, one can attach one end of the resistance band to another part of the body and essentially pull the band at each end. This works well for some exercises but not for others. Ideally, the resistance band needs a secure item to which it can attach. The present invention fulfills that need. While it is possible to secure one end of a resistance band by standing on it, the present invention eliminates this need.

Further, resistance bands are typically tied to an immovable object in order for one to complete the exercises. The present invention is an improvement over the prior art by providing a working device that will secure an end of a resistance band to any metallic surface. This means that one can secure a resistance band to a floor, a steel beam, or even a roof or overhang. This allows one to exercise in a 360 degree range of motion. All that is needed is a metallic surface of sufficient size to which the present invention can adhere.

As stated above, one does not have to physically stand on the resistance band to secure it in place during exercise. The invention claimed here solves this problem. Once the device is affixed to a metal surface of significant weight. The invention becomes the anchoring place for the resistance bands. Also, the present invention will allow one to reproduce multiple exercise configurations such as boxing, mixed martial arts, track and field, football, etc. These differing exercises allow one to focus on different aspects and different muscle groups or different goals from the training session. Further, the present invention allows one to participate in strength training, endurance training, promotion of joint health including increasing range of motion, or many other types of physical exercise.

BRIEF SUMMARY OF THE INVENTION

The present invention relates to the field of exercise equipment. More specifically, the present invention relates to the field of exercise equipment used for resistance training. The present invention allows one to attach a resistance band to the invention and secure the invention to any metal surface, thereby providing a rigid support that provides resistance as one pulls the resistance band. More particularly, the magnetic anchor exercise device provides an attachment point to anchor resistance bands to a metallic structure. The invention includes a series of magnets that work as a freestanding anchor to serve as a counter weight to allow a user to temporarily affix the device and resistance bands to a metal surface. In a preferred embodiment, the invention is made from an industrial grade rubber, carbon fiber, or stainless steel and a series of permanent magnets which may be outfitted with biometric sensors affixed to an upper wheeled axle.

In a preferred embodiment, the present invention is a magnetic anchor that may include a computer chip and/or a set of biometric informative sensors as well as a base that is manufactured with a hole in the base. The base can be configured to accept a force sensor to provide real-time biomechanical analytics to the user. Underneath the surface of the base are one or more magnets secured to the bottom of the invention's base. The invention has a post that has a bottom end configured to be a ball joint. The ball joint is attached to the base of the invention such that the post can rotate in any direction based upon forces exerted on the post. The ball joint provides the ability for the post to move while the base of the invention stays affixed to a metal surface by the magnets. The post extends from the ball joint through the hole in the base and has an attachment point on the top end. Thus, the post begins with a ball joint and ends with an attachment point. It should be appreciated that the attachment point can be any conventional attachment device. In a preferred embodiment the attachment point is a pulley.

In addition, the present invention can be manufactured to have multiple holes through the base and have multiple posts, each with a ball joint and an attachment point. This allows one to attach multiple resistance bands, each of which could rotate freely from one another due to the configuration of the ball joint. This embodiment would be contemplated to also include multiple attachment points to the posts, for ease of securing resistance bands or other devices.

For esthetic purposes, the invention can be configured to include a retainer affixed to the base. The retainer would provide a cover to obstruct the edges of the base from view. The retainer could also serve to protect the base and the magnets under the base from impact should the invention be dropped or bumped by a weight.

The present invention can further include a coupler affixed to the post so that the coupler can separate the attachment point, whether a pulley or hook or other device, from a spring placed around the post. It is contemplated that the coupler can slide along the post to control resistance on the invention itself. The spring is configured to place tension between the coupler at the top of the post and the ball joint at the base of the post. There can also be included a grommet and a nut, where the grommet abuts the coupler and the nut is configured to slide up and down the post. In a preferred embodiment a screw passes through the nut and provides a means for securing the nut to the post thereby controlling the pressure and compression on the spring.

In addition, the present invention would include multiple posts for attaching multiple resistance bands or other devices. In a multi-post configuration, the post would be replaced by an eyed T-bar that would have the same type ball joint on the bottom securing it to the base of the invention, but the top of the T-bar would be configured to accept axles that would stick out perpendicularly from the section of the T-bar that was attached to the ball joint. The axles would pass into the eye at the top of the T-Bar and extend outward from the eye in opposite directions. The axles would be configured such that each can rotate independently of the other. Thus, it becomes possible to attach multiple resistance bands to the invention so that each resistance band can move independently of the other band. I should be appreciated that this configuration can be expanded to include multiple attachment points for resistance bands. Thus, it is contemplated that this configuration of the invention can be manufactured to include four posts, each with an attachment point so that one can attach four separate resistance bands, one for each limb.

The present invention is also contemplated to have the ability to collect data regarding the usage of the device. For example, the invention can be configured to collect information regarding the number of times the post moves, thus indicating the number of repetitions of the pulling exercise occurred. Further, the device can be configured to collect data on the amount of force used on the spring. Also, data can be collected on the range of motion the ball joint progressed. Thus, the present invention can be configured to include visual counters, computer chips, sensors, or any other device that will collect data for later analysis by the user. The present invention is contemplated to include means for collecting biometric data as the device is used, and means for communicating the collected data to the user or a computer or other device for analysis.

The present invention can also be configured with multiple computer chips or sensors for collecting multiple sets of data. Thus, the present invention would include one or more sensors attached to or configured to collect data from one or more points on the magnetic anchor. The sensor could be as simple as a ticker counter that would show the number of times the post moved, or as complex as a computer sensor connected to a computer chip to measure such data as speed, rotation, resistance, angle of deflection, tension, or any other physical manifestation of movement. Thus, the present invention can track the exercises of the user and provide feedback regarding the quantity and quality of exercise. The computer chip can collect the data and process it immediately or preserve the data or download it to another device for analysis of the biometric data. In a preferred embodiment, the present invention would be configured to contain a port in the base to accept the computer chip or sensor.

Still further objectives and advantages to the present invention will become apparent to those skilled in the art from consideration of the following figures and detailed description of a preferred embodiment of the invention.

BRIEF DESCRIPTION OF THE SEVERAL VIEWS OF THE DRAWING(S)

Preferred embodiments of the present invention are illustrated in the drawings.

DETAILED DESCRIPTION OF THE INVENTION

Figure 1:
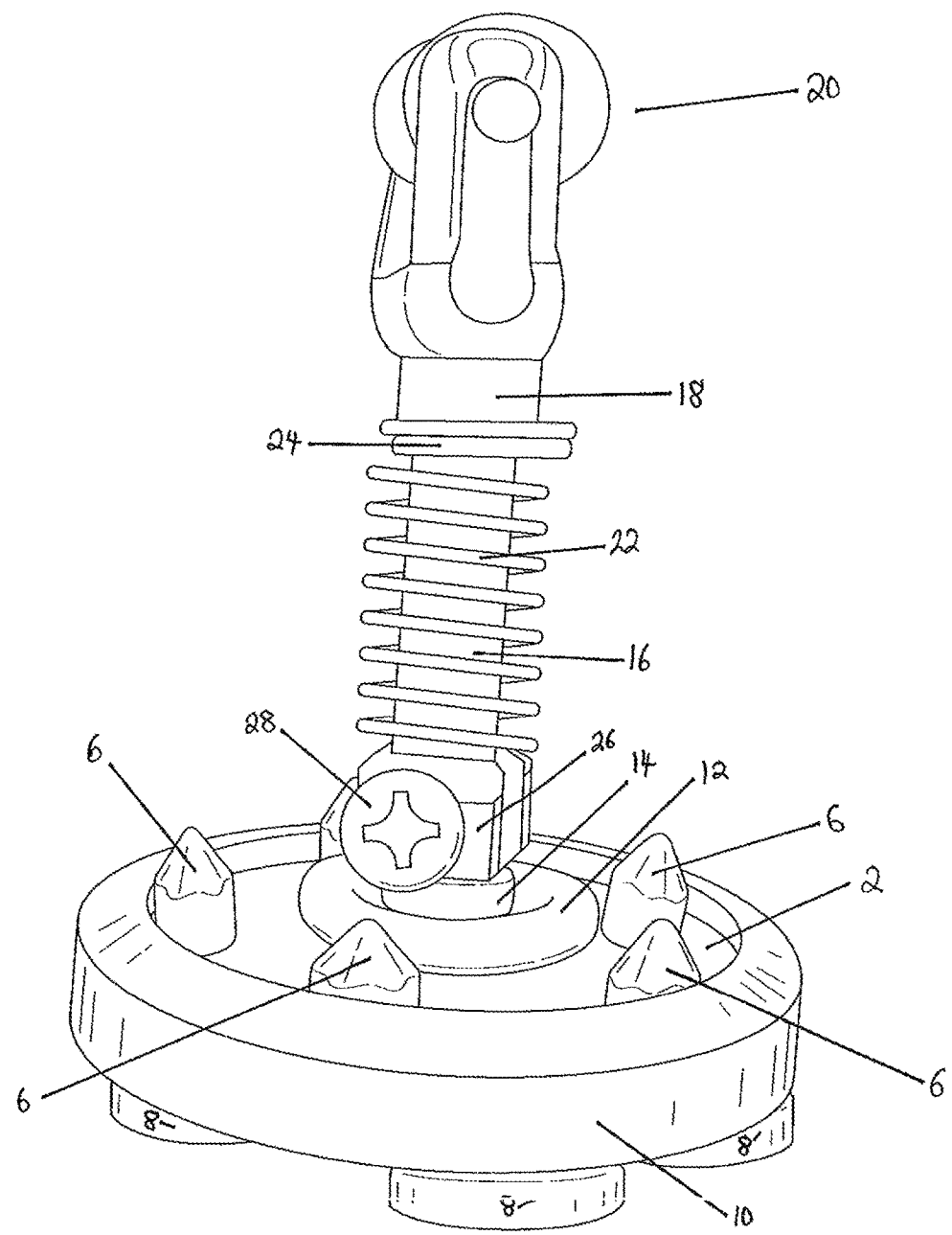
FIG. 1 is a perspective view of a preferred embodiment of the present invention.

Referring now to FIG. 1 a preferred embodiment of the magnetic anchor is shown. The magnetic anchor has a base 2 manufactured to have a plurality of holes 4 (not shown) through the base 2 such that a bolt 6 can pass through. The bolt 6 can be a standard bolt or a screw or any other fastener that can pass through the hole 4 in the base 2. The bolt 6 is removably affixed to a magnet 8 such that the magnet 8 is below the base 2 and secured to the bottom of the base 2 by the bolt 6. It should be appreciated by those skilled in the art that the magnet 8 can be of varying size and strength, although it is generally contemplated that in a preferred embodiment the magnet 8 should be sufficiently strong to adhere to a metal surface with enough force to provide resistance to removal. It should also be understood that the number of magnets 8 used is only limited by the number of holes 4 passing through the base 2. Thus, it is possible to configure the anchor to use fewer magnets 8 than holes 4, if one desires.

Attached to the base 2 is a retainer 10 configured to encapsulate the base 2 and provide an attractive alternative to simply showing the machined edge of the base. It should be appreciated that the retainer 10 can be manufactured from different materials, such as chrome, carbon fiber, stainless steel, or plastic, and painted or dyed varying colors. Further, the retainer 10 can be shaped in different ways.

In the center of the base 2 is a ringed hole 12 that is configured to accept a ball joint 14 affixed to a post 16 extending upwardly from the ball joint 14 and terminating in a coupler 18. The ball joint 14 is configured to allow rotational movement of the post 16. The coupler 18 is affixed to the post 16 and configured to accept a pulley 20 for attaching a resistance band (not shown). It should be appreciated that the coupler 18 is configured to accept other attachments, such as a hook or loop (not shown), depending on the desires of the user and the exercise to be performed.

The anchor can be configured such that the coupler 18 is slidingly engaged to the post 16 such that the coupler 18 can move up and down the post 16 as the pulley 20 is pulled and/or pushed. In order to maintain resistance on the pulley 20 a spring 22 is disposed between a grommet 24 that is between the coupler 18 and the top of the spring 22. The bottom of the spring 22 abuts a nut 26. In an alternative configuration, the nut 26 can be manufactured to slide up and down the post 16. In this configuration, the coupler 18 is affixed to the post 16 such that the coupler 18 is prevented from moving up the post 16 at a certain point and can slide down the post 16 when force is exerted against the pulley 20. The spring 22 controls the movement of the coupler 18 and the pulley 20 and provides resistance to the movement. The nut 26 can be configured to accommodate a screw 28 that provides the ability to secure the nut 26 to the post 16 in order to compress the spring 22. Thus, the amount of compression, and therefore the resistance to further compression and movement, of the spring 22 can be controlled by the nut 26.

Figure 2:
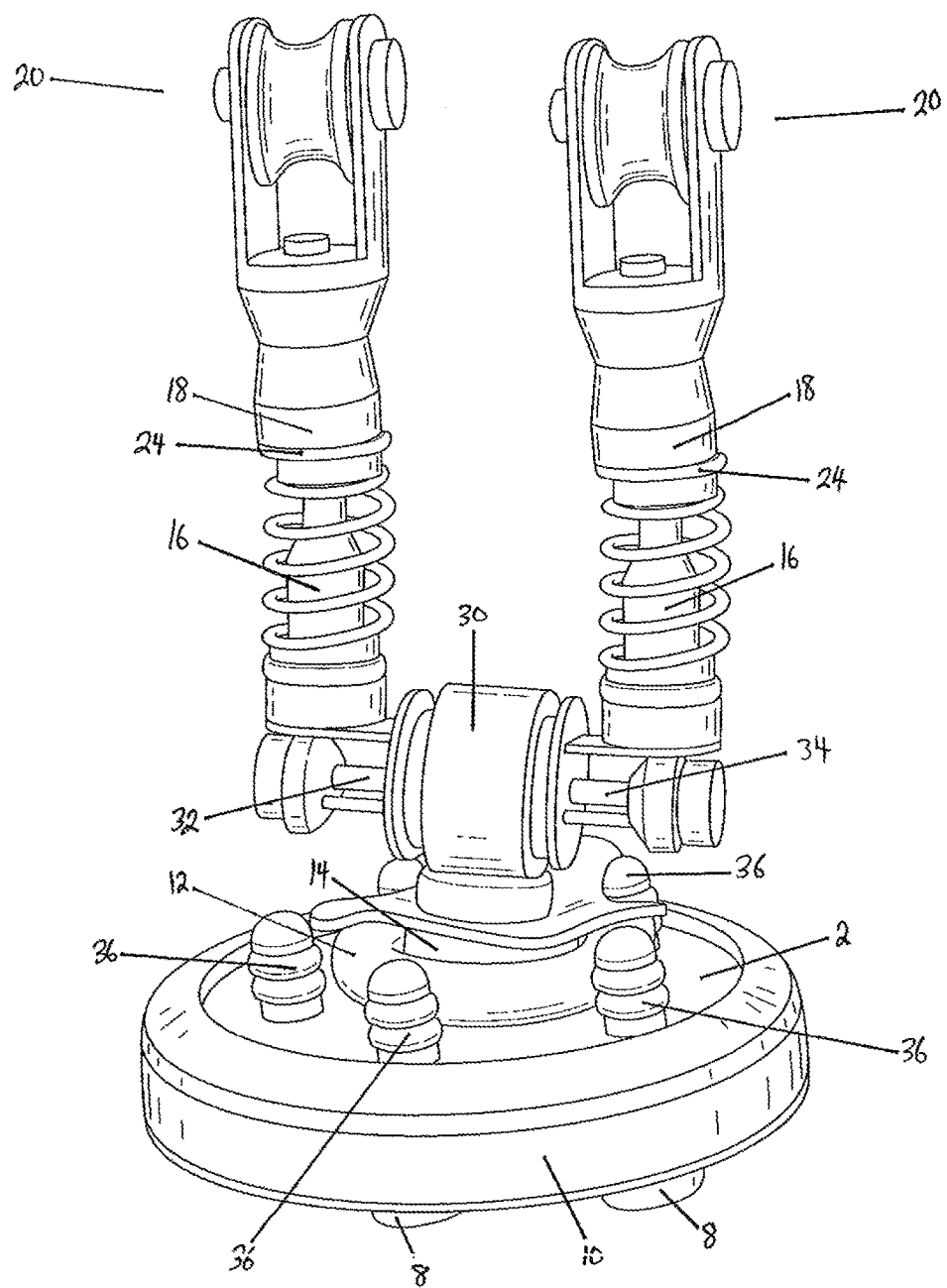
FIG. 2 is a perspective view of an alternate embodiment of the present invention.

Referring now to FIG. 2, an alternative embodiment of the present invention is shown. The basic operation of the invention remains the same, but an additional attachment point is provided. The post 16 is replaced with an eyed T-bar 30 extending upwardly through the ringed hole 12 in the base 2. The T-bar 30 is configured to include the ball joint 14 at the bottom and an eye into which a first axle 32 is attached on one side and a second axle 34 is attached on the opposite side. The first axle 32 and the second axle 34 are each affixed to the eyed T-bar 30 such that the first axle 32 and the second axle 34 can rotate independently of each other. The first axle 32 and the second axle 34 are attached to a post 16. The post 16 is configured as described and shown in FIG. 1. Thus, since the ball joint 14 provides the ability for the eyed T-bar 30 to rotate and the first axle 32 and the second axle 34 each provide the ability for the post 16 and the pulley 20 to rotate, a full range of rotational motion is achieved. Also shown in FIG. 2 are lock nuts 36 used to affix the magnets 8 to the base 2. It should be appreciated that the anchor can be configured to contain any number of posts 16 ending in the pulley 20 or other attachment. Thus, an anchor can be configured with four posts 16 such that a person can use four resistance bands on the same anchor and attach the resistance bands to his or her left arm, right arm, left leg, and right leg. Because the post 16 can rotate in a full range of motion, the movement of the each post 16 is independent from the other posts 16.

Figure 3:
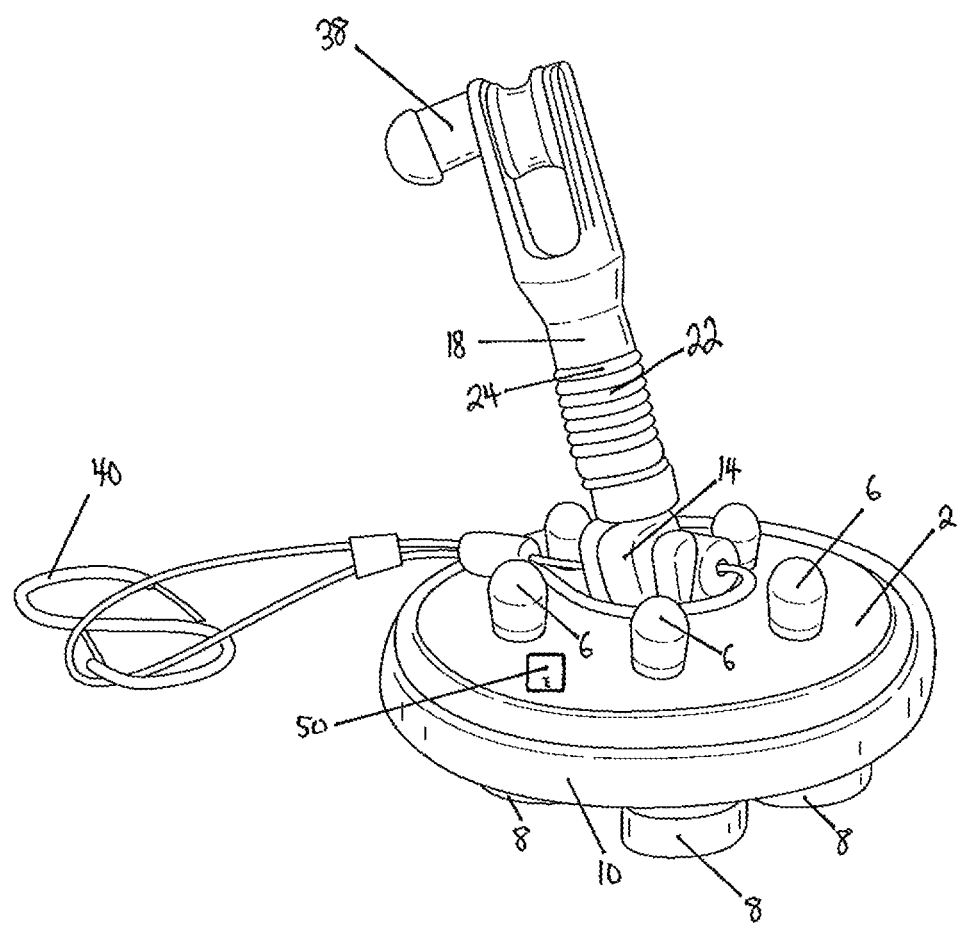
FIG. 3 is a perspective view of another embodiment of the present invention.

Turning now to FIG. 3, another embodiment of the invention is shown. In addition to the pulley 20, this anchor is configured to have an arm 38 protruding out from the pulley 20 to provide another attachment point for a resistance band, hook, or other exercise device. Also, this anchor is configured to allow a lanyard 40 to pass through a ring 42 affixed to or configured into the base 2. This allows one to use the lanyard 40 as a convenient method of transporting the anchor. The base 2 in this embodiment is configured to have a port 50 where a computer chip (not shown) may be inserted to collect biometric or other data from the magnetic anchor 44. It should be appreciated by those skilled in the art that the magnetic anchor 44 can be wired with sensors (not shown) or other means for collecting information which is used to determine and make biometric analyses of the data.

Figure 4:
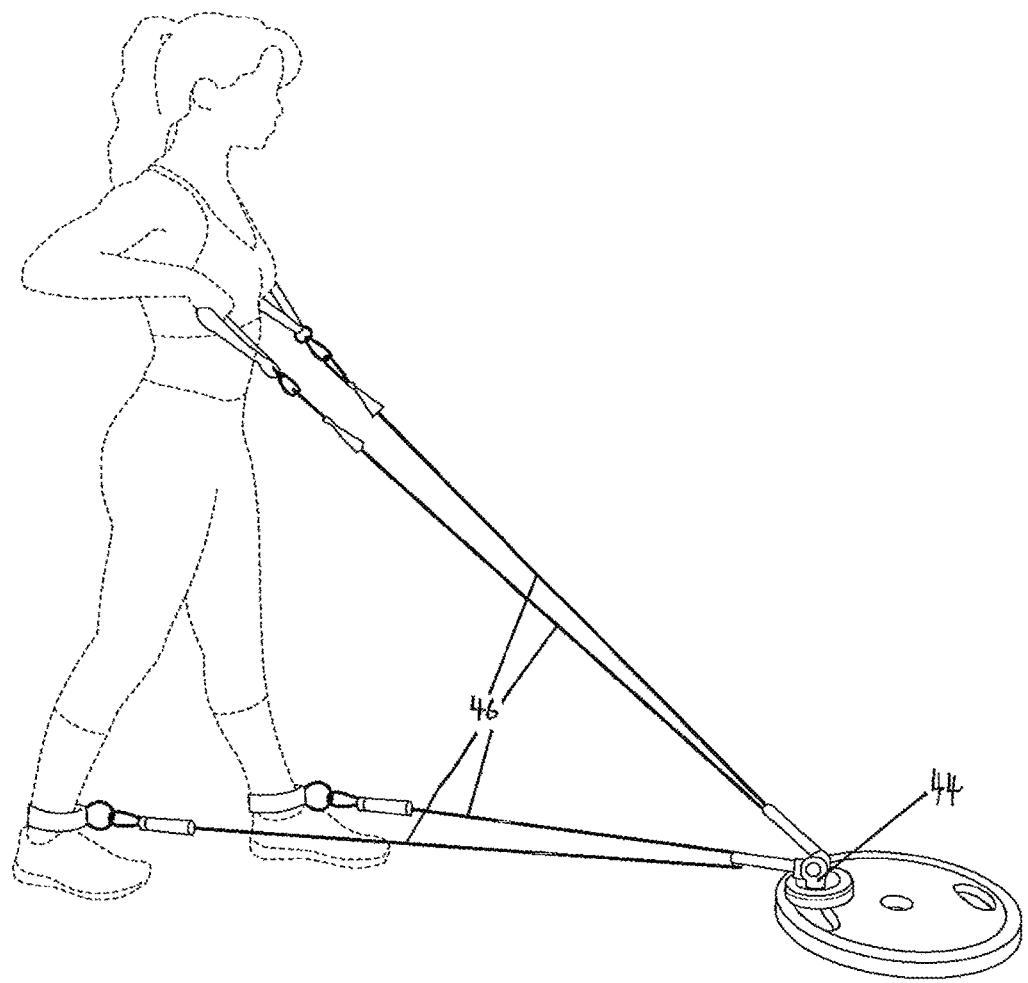
FIG. 4 is a perspective view of the invention in use.

FIG. 4 shows the magnetic anchor in use in a preferred embodiment. The magnetic anchor 44 is attached to a metal weight by the magnets 8. The user attaches resistance bands 46 to the anchor 44 via the pulley 20 or arm 38. Pulling the resistance bands exerts force on the anchor which is prevented from moving because it is attached to the weight. If the user exerts enough force to overcome the inertia of the weight, the weight will start to slide.

The foregoing presents a preferred embodiment of the present invention. The preferred embodiment should not be interpreted to define the limits of the present invention, but rather to enable those skilled in the art to appreciate a preferred embodiment. The present invention is not limited to the described embodiment, and those skilled in the art should appreciate that the present invention can be practiced with varying modifications to the above disclosure without departing from the principles and spirit of the invention. Thus, the present invention is defined and limited by the following claims and their equivalents.

The invention claimed is:

1. A magnetic anchor comprising:
    a base;
    a retainer affixed to said base;
    a hole in said base;
    a magnet secured to the bottom of said base such that said magnet is exposed at the bottom of the magnetic anchor for abutment against a surface to securely attach said base to said surface;
    a post secured to said base by a ball joint, said post extending upwardly through said hole and terminating in an attachment point configured to accept an exercise attachment;
    a coupler affixed to said post configured to accept the exercise attachment wherein said coupler is slidingly engaged to said post;
    a spring disposed between a grommet and a nut, said grommet abutting said coupler, wherein said nut is configured to slide up and down said post;
    a screw passing through said nut and securing said nut to said post in order to compress said spring.

2. The magnetic anchor of claim 1 further comprising:
    a plurality of holes through said base;

a plurality of bolts passing through said holes in said base,
a plurality of magnets, affixed to said plurality of bolts;
a pulley affixed to the end of said post.

3. The magnetic anchor of claim 1 wherein said attachment point is a hook.

4. The magnetic anchor of claim 1 further comprising:
means for collecting data as the device is used;
means for communicating said data for analysis, wherein said means for communicating said data for analysis is a port in the base configured to accept a computer chip or sensor.

5. The magnetic anchor of claim 1 further comprising:
a sensor configured to collect data from one or more points on the magnetic anchor, said sensor configured to communicate said data by visual means.

6. The magnetic anchor of claim 5 further comprising:
additional sensors configured to communicate data collected from the magnetic anchor to a computer chip for preservation and later analysis of said data.

7. The magnetic anchor of claim 4 wherein said means for collecting data is a computer chip and said base is configured to accept said computer chip.

\* \* \* \* \*